United States Patent [19]
Groen et al.

[11] Patent Number: 6,072,068
[45] Date of Patent: Jun. 6, 2000

[54] 16-HYDROXY-11-(SUBSTITUTED PHENYL)-ESTRA-4,9-DIENE DERIVATIVES

[75] Inventors: Marinus Bernard Groen, Oss; Ronald Gebhard, Megen, both of Netherlands

[73] Assignee: Akzo Nobel N.V., Arnhem, Netherlands

[21] Appl. No.: 09/341,603

[22] PCT Filed: Jan. 13, 1998

[86] PCT No.: PCT/EP98/00377

§ 371 Date: Jul. 14, 1999

§ 102(e) Date: Jul. 14, 1999

[87] PCT Pub. No.: WO98/31702

PCT Pub. Date: Jul. 23, 1998

[30] Foreign Application Priority Data

Jan. 15, 1997 [EP] European Pat. Off. .............. 97200098

[51] Int. Cl.[7] ....................... C07D 211/68; C07D 211/78; C07C 255/50; C07C 49/115; C07C 303/00

[52] U.S. Cl. ................ 558/54; 546/286; 546/285; 558/411; 558/429; 565/326

[58] Field of Search ................... 546/285, 286; 558/411, 429, 54; 568/326

[56] References Cited

FOREIGN PATENT DOCUMENTS 0 190 759  8/1986  European Pat. Off. .
33 07 143  9/1983  Germany .

*Primary Examiner*—Joseph McKane
*Assistant Examiner*—Joseph Murray
*Attorney, Agent, or Firm*—Mark E. Gormley

[57] ABSTRACT

The present invention relates to certain 16-hydroxy-11-(substituted phenyl)-estra-4,9-diene derivatives, to processes for their preparation, to pharmaceutical formulations containing them and to their use in medicinal therapy, particularly in the treatment or prophylaxis of glucocorticoid dependent diseases or symptoms.

10 Claims, No Drawings

16-HYDROXY-11-(SUBSTITUTED PHENYL)-ESTRA-4,9-DIENE DERIVATIVES

This application is a 371 of PCT/EP98/00377 filed Jan. 3, 1998.

FIELD OF THE INVENTION

The present invention relates to certain 16-hydroxy-11-(substituted phenyl)-estra4,9-diene derivatives, to processes for their preparation, to pharmaceutical formulations containing them and to their use in medical therapy, in particular in the treatment or prophylaxis of glucocorticoid-dependent diseases.

BACKGROUND OF THE INVENTION

U.S. Pat. No. 5,089,635 discloses certain 13-alkyl-11β-phenyl-gonanes having antigestagenic and antiglucocorticoid effects. European patent specification No. 0,057,115 discloses 19-nor steroids and 19-nor-D-homo steroids having anti-glucocorticoid activity.

A number of 16-hydroxy-11-(substituted phenyl)-estra-4,9-diene derivatives have now been found which have a highly selective affinity to glucocorticoid receptors and have potent in vivo anti-glucocorticoid activity.

SUMMARY OF THE INVENTION

Accordingly, the present invention provides compounds of formula I

I wherein $R_1$ is $C_{1-6}$alkyl, $C_{3-6}$cycloalkyl, $C_{1-6}$alkoxy, triflate, pyridyl or phenyl where the phenyl moiety is optionally substituted by one or more substituents selected from cyano, halogen and $C_{1-4}$alkyl;

$R_2$ is hydrogen, $C_{1-6}$alkyl, 1-oxo-$C_{1-6}$alkyl or carboxy-1-oxo-$C_{1-6}$alkyl;

$R_3$ is hydrogen, halogen or $C_{1-6}$alkyl optionally substituted by one or more substituents selected from $C_{1-6}$alkoxy and halogen;

$R_4$ is hydrogen, $C_{1-6}$alkyl, 1-oxo-$C_{1-6}$alkyl or carboxy-1-oxo-$C_{1-6}$alkyl; and X is (H,OH), O or NOH;

or a pharmaceutically acceptable salt or solvate thereof.

The present invention includes the 16-hydroxy-11-(substituted phenyl)-estra-4,9-diene derivatives of formula I wherein:

1. $R_1$ is phenyl, triflate, or $C_{1-6}$alkyl, for example, t-butyl, isopropyl or methyl.
2. $R_2$ is hydrogen.
3. $R_3$ is hydrogen, halogen, for example, chloro, $C_{1-6}$alkyl, for example, methyl, ethyl, propyl or t-butyl optionally substituted by $C_{1-6}$alkoxy, such as methoxy.
4. $R_4$ is hydrogen or methyl.
5. X is O.
6. $R_1$, $R_2$, $R_3$, $R_4$ and X are as defined in points 1 to 5 supra or a pharmaceutically acceptable salt or solvate thereof.
7. $R_1$ is $C_{1-6}$alkyl, $C_{3-6}$cycloalkyl, triflate or phenyl; $R_2$ is hydrogen, $C_{1-6}$alkyl, 1-oxo-$C_{1-6}$alkyl or carboxy-1-oxo-$C_{1-6}$alkyl; $R_3$ is hydrogen, halogen or $C_{1-6}$alkyl optionally substituted by one or more substituents selected from $C_{1-6}$alkoxy and halogen; $R_4$ is hydrogen, $C_{1-6}$alkyl, 1-oxo-$C_{1-6}$alkyl or carboxy-1-oxo-$C_{1-6}$alkyl; and X is (H,OH), O or NOH; or a pharmaceutically acceptable salt or solvate thereof.

Further examples of compounds of formula I above include examples 1 to 4.

As used herein the term alkyl means a straight or branched chain alkyl group. Such alkyl groups include methyl, ethyl, i-propyl, n-propyl, n-butyl, s-butyl, t-butyl, n-pentyl, isopentyl, neopentyl, n-hexyl, isohexyl and neohexyl. Reference to cycloalkyl includes cyclopropyl, cyclopentyl and cyclohexyl.

The term alkoxy has the meaning as understood by the person skilled in the art and includes straight and branched chains. Examples of alkoxy groups include methoxy and ethoxy. Preferred alkoxy groups include $C_{1-4}$alkoxy.

The term halogen includes chloro, bromo, fluoro and iodo.

Triflate means trifluoromethanesulphonate.

1-oxo-$C_{1-6}$alkyl or carboxy-1-oxo-$C_{1-6}$alkyl groups include 1-oxo-methyl, 1-oxo-ethyl, 1-oxo-propyl, 3-carboxy-1-oxopropyl, 3-carboxy-1-oxobutyl and 3-carboxy-1-oxopentyl.

DETAILED DESCRIPTION OF THE INVENTION

Preferred examples of $R_1$ are phenyl and $C_{1-6}$alkyl, for example, t-butyl (1,1-dimethylethyl), isopropyl (1-methylethyl) or methyl, most preferably t-butyl and phenyl.

$R_2$ is preferably hydrogen.

Preferred examples of $R_3$ include $C_{1-6}$alkyl, most preferably methyl.

$R_4$ is preferably hydrogen or $C_{1-6}$alkyl, in particular methyl.

X is preferably O.

Preferred compounds of formula I include those wherein $R_1$ is phenyl or $C_{1-6}$alkyl, for example, t-butyl, isopropyl or methyl; $R_2$ is hydrogen; $R_3$ is $C_{1-6}$alkyl, most preferably methyl; $R_4$ is hydrogen or $C_{1-6}$alkyl, in particular methyl; and X is O; or a pharmaceutically acceptable salt or solvate thereof.

Particularly preferred 16-hydroxy-11-(substituted phenyl)-estra-4,9-diene derivatives of formula I include:

(11β,16α,17β)-11-(4-t-butylphenyl)-16,17-dihydroxy-17-(1-propynyl)estra-4,9-dien-3-one (11β,16α,17β)-11-(4-isopropylphenyl)-16,17-dihydroxy-17-(1-propynyl)estra-4,9-dien-3-one;

(11β,16α,17β)-11-(4-methylphenyl)-16,17-dihydroxy-17-(1-propynyl)estra-4,9-dien-3-one;

(11β,16α,17β)-11-(1,1'-biphenyl-4-yl)-16,17-dihydroxy-17-(1-propynyl)estra-4,9-dien-3-one;

(11β,16α,17β)-16,17-dihydroxy-11-[4-[(trifluoromethylsulfonyl)oxy]phenyl]-17-(1-propynyl)estra4,9-dien-3-one;

or a pharmaceutically acceptable solvate thereof.

For therapeutic use, salts of the compounds of formula I are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

Salts according to the invention include ammonium salts, alkali metal salts such as those of sodium or potassium, alkali earth metals salts such as those of calcium and magnesium, salts with organic bases such as dicyclohexylamine and N-methyl-D-glucamine, and salts with amino acids, such as arginine and lysine.

Solvates according to the invention include hydrates.

In a further aspect of the invention there are provided the compounds of formula I and their pharmaceutically acceptable salts or solvates for use in therapy, more particularly in the treatment or prophylaxis of glucocorticoid dependent diseases or symptoms such as Cushing syndrome, diabetes, glaucoma, sleep disturbances, depression, anxiety, atherosclerosis, hypertension, adiposity, osteoporosis, addiction and the treatment of the symptoms of withdrawal from substance abuse, for example, narcotics, cocaine and alcohol. The compounds also find use in the treatment of neurodegenerative diseases, such as, Alzheimers and psychotic disorders such as schizophrenia, mania, hyperactivity, substance abuse, emesis and schizophreniaform disorders.

The compounds of formula I and their pharmaceutically acceptable salts and solvates and in particular the preferred compounds described supra are useful for the treatment of depression.

The present invention further includes a method for the treatment of an animal, for example, a mammal including a human, suffering from or liable to suffer from a glucocorticoid dependent disease including any of the aforementioned diseases or symptoms, which comprises administering an effective amount of a compound of formula I or a pharmaceutically acceptable salt or solvate thereof.

In yet a further aspect, the present invention provides the use of a compound of formula I or a pharmaceutically acceptable salt or solvate thereof for the manufacture of a medicament for the treatment or prophylaxis of any of the aforementioned diseases or symptoms.

The amount of a compound of formula I or a pharmaceutically acceptable salt or solvate, also referred to herein as the active ingredient, which is required to achieve a therapeutic effect will, of course, vary with the particular compound, the route of administration, the age and condition of the recipient, and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day and most preferably in the range 0.1 to 10 mg per kilogram body weight per day. The desired dose may be presented as one, two, three, four, five or more sub-doses administered at appropriate intervals throughout the day.

While it is possible for the active ingredient to be administered alone, it is preferable to present it as a pharmaceutical formulation. Accordingly, the present invention further provides a pharmaceutical formulation comprising a compound of formula I or a pharmaceutically acceptable salt or solvate thereof together with a pharmaceutically acceptable carrier thereof and optionally other therapeutic agents. The carrier must be "acceptable" in the sense of being compatible with the other ingredients of the formulation and not deleterious to the recipients thereof.

Formulations include those suitable for oral, rectal, nasal, topical (including transdermal, buccal and sublingual), vaginal or parenteral (including subcutaneous, intramuscular, intravenous, intradermal and intravitreal) administration. The formulations may be prepared by any methods well known in the art of pharmacy, for example, using methods such as those described in Gennaro et al., Remington's Pharmaceutical Sciences (18th ed., Mack Publishing company, 1990, see especially Part 8: Pharmaceutical Preparations and their Manufacture). Such methods include the step of bringing into association the active ingredient with the carrier which constitutes one or more accessory ingredients. Such accessory ingredients include those conventional in the art, such as, fillers, binders, diluents, disintegrants, lubricants, colorants, flavoring agents and wetting agents.

Formulations suitable for oral administration may be presented as discrete units such as pills, tablets or capsules each containing a predetermined amount of active ingredient; as a powder or granules; as a solution or suspension. The active ingredient may also be presented as a bolus or paste, or may be contained within liposomes.

Formulations for rectal administration may be presented as a suppository or enema.

For parenteral administration, suitable formulations include aqueous and non-aqueous sterile injection. The formulations may be presented in unit-dose or multi-dose containers, for example, sealed vials and ampoules, and may be stored in a freeze dried (lyophilised) condition requiring only the addition of the sterile liquid carrier, for example, water prior to use.

Formulations suitable for administration by nasal inhalation include fine dusts or mists which may be generated by means of metered dose pressurised aerosols, nebulisers or insufflators.

The present invention further includes the following processes for the preparation of a compound of formula I or a pharmaceutically acceptable salt or solvate thereof.

The compounds of formula I may be produced by various methods known in the art of organic chemistry in general. Starting materials are either known and readily available from chemical sources or may themselves be produced by conventional techniques.

In the following description the symbols $R_1$, $R_2$, $R_3$, $R_4$ and X have the meanings ascribed to them in formula I unless otherwise stated.

According to a first general process (A), compounds of formula I may be prepared by dehydration and deprotection of a compound of formula II

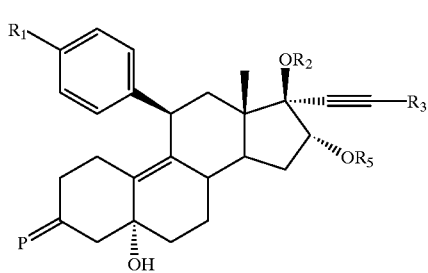

wherein P is a protected keto group and $R_5$ is a group $R_4$ as defined in relation to formula I or a suitably protected $R_4$ group. Suitable protecting groups and methods to remove these groups are known in the art, for example from T. W. Green: Protective Groups in Organic Synthesis (Wiley, N.Y., 1981); Particularly suitable protecting groups for the protection of keto groups are acetals, for example, 1,2-ethylene ketal. Such groups may be removed, for example, by acid hydrolysis.

Dehydration may be carried out using methods known in the art. Typically, the reaction is carried out in the presence of a mineral acid, such as hydrochloric acid or sulphuric acid in a suitable solvent, for example, acetone in a temperature range of −20 to 25° C.

According to a second general process (B), compounds of formula I wherein X is (H,OH) may be prepared by treating a corresponding compound of formula I wherein X is O with a suitable reducing agent. For example, reduction with sodium borohydride in the presence of a solvent such as methanol, typically in a temperature range of 0 to 25° C.

According to a third general process (C), compounds of formula I wherein X is NOH may be prepared by condensation of a compound of formula I wherein X is O with a suitable oximating agent. For example, by treating the corresponding 3-keto compound with hydroxylamine in the presence of a suitable solvent such as pyridine.

Where necessary or desired, following the above process, any one or more of the following further steps in any order may be performed:

(i) converting a compound of formula I into a pharmaceutically acceptable salt or solvate of a compound of formula I;

(ii) converting a pharmaceutically acceptable salt or solvate of a compound of formula I into a compound of formula I; and (iii) converting a pharmaceutically acceptable salt or solvate of a compound of formula I into another pharmaceutically acceptable salt or solvate of a compound of formula I.

A suitable process for the preparation of derivatives of formula II starts with estra-5(10),9(11)-diene-3,17-dione-3-(cyclic 1,2-ethanediyl acetal) which may be prepared using methods described in EP 0683172 or according to the method described herein below in example A. This compound is first converted into the 17-silylenolether using methods well known in the art, for example, by reaction with lithium diisopropylamide and trimethylsilylchloride, immediately followed by reaction with phenyl-trimethylammonium tribromide in pyridine. The resulting 16α-bromo derivative is subsequently converted with sodium hydroxide in water and pyridine according to the procedure described in the J. Am. Chem. Soc. 102, 5402 (1980), into the corresponding 3-protected 16α-hydroxysteroid. Alkynylation at C17 followed by (optional) protection of the 16-hydroxy function (e.g. as TBDMS-ether see T. W. Green: Protective Groups in Organic Synthesis, Wiley, N.Y., 1981) and epoxidation of the 5(10) double bond (e.g. with hydrogen peroxide, trifluoroacetophenone and pyridine in dichloromethane according to EP 0298020) provides the 16-hydroxy(protected)-3-ketoprotected 5α,10α-epoxy-17α-alkynyl-17β-hydroxy-estr-9(11)-en-3-one. A copper catalyzed Grignard reaction with this epoxide eventually leads to compounds of formula II.

In the alternative, compounds of formula II may conveniently be prepared using estra-5(10),9(11)-diene-3,17-dione-3-(cyclic 1,2-ethanediyl acetal) as a starting material as herein before described. This compound may be converted into the corresponding 5α10α-epoxide e.g. with hydrogen peroxide, trifluoroacetophenone and pyridine in dichloromethane according to the procedure described in EP 0298020. A copper catalyzed Grignard reaction provides the corresponding 3-protected-11-aryl-5-hydroxy-estr-9,10-en-17-one. Subsequent conversion into the 17-enol silylderivative (by treatment with LDA and trimethylsilylchloride) followed by bromination with phenyl-trimethylammonium tribromide in pyridine provides the corresponding 16-bromide. The desired 16α-hydroxy function is introduced by nucleophilic substitution [sodium hydroxide, pyridine/water, according to the procedure described in J. Am. Chem. Soc. 102, 5402 (1980)]. Propynylation (propyne, n-BuLi) finally leads to the desired compound II.

Compounds of formula I may be converted into a pharmaceutically acceptable 1-oxo-$C_{1-4}$alkyl or carboxy-1-oxo-$C_{1-4}$alkyl by reaction with an appropriate esterifying agent, for example, by treatment with an appropriately activated carboxylic acid, like for example an acid chloride, or an activated dicarboxylic acid, like for example a cyclic anhydride, using methods well known in the art.

The compounds of formula I, may be converted into pharmaceutically acceptable salts thereof in a conventional manner, for example by treatment with the appropriate acid.

The present invention further includes all novel intermediates defined herein and in particular compounds of formula II.

Particularly preferred intermediates include:

5α,16α,17β-trihydroxy-11β-[4-t-butylphenyl]-17α-propynyl-estr-9-en-3-one 3-(cyclic 1,2-ethanediyl acetal);

5α,16α,17β-trihydroxy-11β-[4-t-butylphenyl]-17α-pentynyl-estr-9-en-3-one 3-(cyclic 1,2-ethanediyl acetal);

5α,16α,17β-trihydroxy-11β-[4-t-butylphenyl]-17α-hexynyl-estr-9en-3-one 3-(cyclic 1,2-ethanediyl acetal);

5α,17β-dihydroxy-11β-[4-t-butylphenyl]-16α-methoxy-17α-propynyl-estr-9-en-3-(cyclic 1,2ethanediyl acetal);

21-chloro-11-(4-t-butylphenyl)-5α,16α,17β-trihydroxy-19-norpregn-9-en-20-yn-3-one 3-(cyclic 1,2-ethanediyl acetal);

or a pharmaceutically acceptable salt or solvate thereof.

The following examples are intended for illustration only and are not intended to limit the scope of the invention in any way.

EXAMPLE A

Estra-5(10),9(11)-diene)-3,17-dione 3,3-ethyleneketal

A mixture of 500 ml of cyclohexane, 183 ml of triethyl orthoformate, 92 ml of ethylene glycol and 0.9 g of p-toluenesulphonic acid was stirred for 30 minutes at room temperature and thereafter heated to reflux. The formed ethanol was together with cyclohexane distilled off but the volume was kept constant by addition of cyclohexane. After 4.5 hours the residue of cyclohexane was distilled off and 1 eq. of the residue was added as a water scavenger under an atmosphere of nitrogen to 1 g of estra-4,9diene-3,17-dione, 0.1 eq. of hydrogen chloride in dioxane and 1.5 eq. of ethylene glycol in 15 ml of dimethoxyethane at −10° C. After 75 min. the reaction mixture was poured into a saturated aqueous solution of sodium hydrogen carbonate. The crystal mass was filtered off, washed with water and dried in vacuo, after which 1.1 g of estra-5(10),9(11)-diene-3,17 dione 3,3-ethyleneketal was obtained. After crystallisation from ethanol 1 g of product was obtained having a purity of better than 97%.

Example 1

(11β,16α,17β)-11-(4-t-butylghenyl)-16,17-dihydroxy-17-(1-progynyl)estra-4.9-dien-3-one a) 16-bromo-estra-5(10),9(11)-diene-3,17-dione-3-(cyclic1,2-ethanediyiacetal)

A solution of 192 mmol LDA (prepared by adding 120 ml of a 1.6 M n-BuLi solution to a solution of 34 ml diisopropylamine in 340 ml of dry THF) was added dropwise to a cold (−30° C.) solution of 50 g (159 mmol) of estra-5(10),9(11)-diene-3,17-dione-3-(cyclic 1,2-ethanediyl acetal) in 480 ml dry THF. Stirring was continued for 15 min. at −30° C. Then, 60 ml (473 mmol) of trimethylsilylchloride was added dropwise and the solution was allowed to warm to 0° C. over ca. 1 hour. Phenyl-trimethylammonium tribromide (60 g, 160 mmol), dissolved in 60 ml pyridine, was slowly added to this solution of the enol ether and after one hour the reaction mixture was warmed to room temperature. TLC indicated complete disappearance of the starting material and the formation of a more lipophilic product (toluenelethyl acetate; 85/15). Work-up was accomplished by pouring the reaction mixture into a cold ammonium chloride solution followed by extraction with dichloromethane. Drying with magnesium sulfate, filtration and evaporation of the solvents gave a semi-solid mass. Crystallisation from ethanol gave 41.8 g of the desired bromide (predominantly alpha) as off-white crystals (m.p. 166.8–167.8° C.).

b) 16α-hydroxy-estra-5(10),9(11)-diene-3,17-dione-3-(cyclic 1,2ethanediyl acetal)

40 g (101 mmol) of the product obtained under a) was dissolved in 840 ml dry pyridine. Under stirring, 240 ml water was added, followed by 120 ml of a 1N NaOH solution. The temperature was kept below 25° C. After stirring for 30 min. at room temperature, TLC indicated complete conversion. The mixture was poured into a saturated ammonium chloride solution. Extraction with dichloromethane, drying with magnesium sulfate and evaporation of the solvents provided the crude hydroxy compound as an oil. Column chromatography (silica gel, heptanelethyl acetate 8/2) provided 18.8 g. of the pure 16α-hydroxy-estra-5(10),9(11)-diene-3,17dione-3-(cyclic 1,2-ethanediyl acetal) as a foam. An analytical sample, crystallized from diethyl ether, afforded white crystals; m.p. 188.4–190.6° C.

c) 16α,17β-dihydroxy-17α-propynyl-estra-5(10),9(11)-diene-3,17-dione-3-(cyclic 1,2-ethanediyl acetal)

Into a three-necked flask, equipped with a gas-inlet tube and a dropping funnel containing 130 ml dry THF at −70° C., was added 106 ml of a 1.6 N n-BuLi solution in hexane. The solution turned yellow. Propyne gas was bubbled through this solution until the yellow colour disappeared. A white suspension had formed and stirring was continued for 15 min at −70° C. Then, a solution of 18 g (54.3 mmol) of the previously obtained product, dissolved in 150 ml dry THF, was added dropwise to the cold solution of the propyne anion. After addition, the solution was allowed to warm slowly to −20° C. After stirring for 2 hrs at that temperature, TLC indicated complete conversion of the starting material. Work-up was accomplished by pouring the mixture into a saturated ammonium chloride solution, followed by extraction with dichloromethane. Drying with magnesium sulfate and evaporation of the solvents provided 19.8 g of the crude material. Purification using a short column (silica gel, heptane/ethyl acetate 1/1) provided 15.9 g of the desired pure compound. Crystallization of an analytical sample from diethyl ether afforded white crystals, m.p. 71° C.

d) 16-TBDMS ether of 16α,17β-dihydroxy-17α-propynyl-estra-5(10),9(11)-diene-3,17-dione-3-(cyclic 1,2-ethanediyl acetal)

15.9 g (42.9 mmol) of the product obtained under c) was dissolved in 60 ml dry DMF. To this solution, 15 g imidazole was added followed by 15 g (120 mmol) of t-butyldimethylsilylchloride. After stirring for 3 hrs at 40° C., TLC analysis indicated a quantitative conversion of the starting compound into one lipophilic product. The mixture was quenched with ammonium chloride solution, followed by extraction with dichloromethane. Drying with magnesium sulfate, followed by evaporation of the solvents afforded 35 g of the crude silyl compound which was used as such in the next step.

e) 16-TBDMS-ether of 5α,10α-epoxy-17α-propynyl-17β-hydroxy-estr-9(11)-en-3one-3-(cyclic-1,2-ethanediyl acetal)

35 g of the crude product obtained under d) (maximum amount of pure compound 20.8 g, 42.9 mmol) was dissolved in 300 ml of dichloromethane; subsequently 2 ml of pyridine, 5.3 ml of trifluoroacetophenone and 70 ml of 30% hydrogen peroxide were added and the resulting two-phase system was vigorously stirred at ambient temperature for 48 hours. The mixture was poured into water and the organic layer was separated and washed twice with saturated sodium thiosulfate solution. Drying with anhydrous magnesium sulfate, filtering and evaporation provided a semi-solid residue. Purification with column chromatography provided 16.4 g of the desired a-epoxide as amorphous material.

f) 16-TBDMS-ether of 5α,16α,17β-trihydroxy-11β-[4-t-butylphenyl]-17α-propynyl-estr-9-en-3one 3-(cyclic 1,2-ethanediyl acetal)

330 mg of CuCl were added at 0–5° C. to a solution of 4-t-butylphenylmagnesium bromide (prepared from 0.83 g (35 mmol) Mg and 6.0 ml (34.5 mmol) 4-bromo-t-butylbenzene in 50 ml dry THF). After stirring for 30 min. at 0–5° C., 2.5 g (5 mmol) of the previously obtained epoxide, dissolved in 30 ml dry THF were added dropwise, while keeping the temperature below 10° C. Stirring was continued for one hour at ambient temperature. Work-up was accomplished by pouring the mixture into a saturated ammonium chloride solution and extraction with ethyl acetate (2×). The combined organic layers were washed with brine, dried with anhydrous magnesium sulfate, filtered and concentrated. Column chromatography (silica gel, heptane/ethyl acetate 7/3) provided 2.7 g of the pure 11-substituted compound as white amorphous material.

g) (11β,16α,17β)-11-(4-t-butylphenyl)-16,17-dihydroxy-17-(1-propynyl) estra-4,9-dien-3-one 2.7 gr (4.26 mmol) of the compound obtained under f) was dissolved in 50 ml acetone. At room temperature 3 ml 6N $H_2SO_4$ was added and the mixture was stirred for two hours. Then, the cold solution was poured into saturated sodium bicarbonate solution and the mixture was extracted with ethyl acetate (2×). The combined organic layers were washed with brine, dried with anhydrous magnesium sulfate, filtered and concentrated. Chromatography (dichloromethane/acetone 8/2) provided 1.6 g of the desired (11β,16α,17β)-11-(4-t-butylphenyl)-16,17-dihydroxy-17-(1-propynyl)estra-4,9-dien-3-one as a white solid. Crystallisation from diethyl ether afforded 1.2 g white crystals, m.p. 251.6–253.8° C.

Alternative Procedure a) 5α,10α-epoxy-estra-9(11)-diene-3,17-dione-3-(cyclic 1,2-ethanediyl acetal)

150 g of estra-5(10),9(11)-diene-3,17-dione-3-(cyclic 1,2-ethanediyl acetal) 478 mmol) was dissolved in 2.2 l of dichloromethane; subsequently 14.4 ml of pyridine, 48 ml of trifluoroacetophenone and 666 ml of 30% hydrogen peroxide were added and the resulting two-phase system was vigorously stirred at ambient temperature for 48 hours. The mixture was poured into water and the organic layer was separated and washed twice with saturated sodium thiosulfate solution. Drying with anhydrous magnesium sulfate, filtering and evaporation provided a semi-solid residue. Crystallisation from ether/heptane afforded 80 g of the desired c-epoxide as white crystalline material (m.p. 153° C.).

b) 5α-hydroxy-11-(4-t-butylphenyl)-estr-9-en-3,17-dione-3-(cyclic 1,2-ethanediyl-acetal)

900 mg of CuCl were added at 0–5° C. to a solution of 20 g (60 mmol) of the previously obtained epoxide dissolved in 30 ml dry THF. The mixture was stirred for 20 min. and slowly a solution of 4-t-butylphenylmagnesium bromide (prepared from 5 g (200 mmol) Mg and 32.8 ml (200 mmol) 4-bromo-t-butylbenzene in 150 ml dry THF), were added dropwise, while keeping the temperature below 10° C. Stirring was continued for one hour at ambient temperature. Work-up was accomplished by pouring the mixture into saturated ammonium chloride solution and extracting with ethyl acetate (2×). The combined organic layers were washed with brine, dried with anhydrous magnesium sulfate, filtered and concentrated. Column chromatography (silica gel, heptane/ethyl acetate 7/3) provided 28 g of the desired 5α-hydroxy-11β-[4-t-butylphenyl]estr-9-ene-3-one 3-(cyclic 1,2-ethanediyl acetal).

c) 16α-bromo-5α-hydroxy-11β-[4-t-butylphenyl]estra-9ene-3-one-3-(cyclic 1,2-ethanediyl acetal)

A solution of 181 mmol LDA (prepared by adding 113 ml of a 1.6 M n-BuLi solution to a solution of 25.6 ml diisopropylamine in 400 ml dry THF) was added dropwise to a cold solution (–60° C.) of 28 g (60 mmol) 5α-hydroxy-11β-[4-t-butylphenyl]-estr-9-en-3-one 3-(cyclic 1,2-ethanediyl acetal) in 700 ml dry THF. Stirring was continued for 30 min at –50° C. Then 38.3 ml of trimethylsilylchloride was added dropwise and the solution was stirred at –45° C. for 1 hour. After cooling the reaction mixture to –60° C., 27.7 g (72.4 mmol) phenyltrimethylammonium tribromide, dissolved in 100 ml pyridine, was added dropwise. After 2 hours stirring at –60° C. TLC indicated complete disappearance of the starting material and the formation of a more lipophilic product (heptane/ethyl acetate; 6/4). Work-up was accomplished by pouring the reaction mixture into ammonium chloride solution, followed by extraction with ethyl acetate. Drying over magnesium sulfate, filtration and evaporation of the solvents gave a semi-solid mass. Crystallisation from heptane, followed by a crystallisation from ethanol gave 20 g of the desired bromide as white crystals (m.p. 164–165° C.).

d) 5α,16α-dihydroxy-11β-[4t-butylphenyl]estr-9-en-3,17-dione-3-(cyclic 1,2-ethanediyl acetal)

12.5 g (23.0 mmol) of the product obtained under a) was suspended in 400 ml 75% pyridine in water. 27.5 ml 1 M NaOH was added. After stirring for 30 min at room temperature the starting compound was dissolved and TLC indicated complete conversion.

The reaction mixture was poured into ammonium chloride solution and extracted with ethyl acetate. Drying with magnesium sulfate, evaporation of the solvents and co-evaporation with toluene provided the crude hydroxy compound. Crystallisation from diisopropyl ether gave 9.0 g of the desired compound (m.p. 180–182° C.).

e) 5α,16α,17α-trihydroxy-11β-[4-t-butylphenyl]-17-(1-propynyl)estr-9-en-3-one-3-(cyclic 1,2-ethanediyl acetal)

Into a three-necked flask, equipped with a gas-inlet tube and a dropping funnel containing 130 ml dry THF at –70° C., was added 95 ml of a 1.6 N n-BuLi solution in hexane. The solution turned yellow. Propyne gas was bubbled through this solution until the yellow colour disappeared. A white suspension had formed and stirring was continued for 15 min at –70° C. Then, a solution of 18 g (38 mmol) of the previously obtained product, dissolved in 150 ml dry THF, was added dropwise to the cold solution of the propyne anion. After the addition, the solution was allowed to warm slowly to –20° C. After stirring for 2 hrs at that temperature, TLC indicated complete conversion of the starting material. Work-up was accomplished by pouring the mixture into saturated ammonium chloride solution, followed by extraction with dichloromethane. Drying over magnesium sulfate and evaporation of the solvents provided 19.8 g of the crude material. Purification using a short column (silica gel, heptane/ethyl acetate 1/1) provided 18.5 9 of the desired pure compound as a white foam.

f) (11β,16α,17β)-11-(4-t-butylphenyl)-16,17-dihydroxy-17-(1-propynyl)-estra-4,9-dien-3-one 2.7 g (4.26 mmol) of the compound obtained under e) was dissolved in 50 ml acetone. At room temperature 3 ml 6N $H_2SO_4$ was added and the mixture was stirred for two hours. Then, the cold solution was poured into saturated sodium bicarbonate solution and the mixture was extracted with ethyl acetate (2×). The combined organic layers were washed with brine, dried over anhydrous magnesium sulfate, filtered and concentrated. Chromatography (dichloromethane/acetone 8/2) provided 1.6 g of the desired (11β,16α,17β)-11-(4-t-butylphenyl)-16,17-dihydroxy-17-(1-propynyl)estra-4,9-dien-3-one as a white solid. Crystallisation from diethyl ether afforded 1.2 g white crystals, m.p. 251.6–253.8° C.

By substitution of the 4-bromo-t-butylbenzene by 4-bromo-isopropylbenzene, 4-bromo-toluene and 4-bromo-biphenyl, the following products have been obtained:

1A. (11β,16α,17β)-11-(4-isopropylphenyl)-16,17-dihydroxy-17-(1-propynyl)estra-4,9-dien-3-one; m.p. 153.4–154.9° C.

1B. (11β,16α,17β)-11-(4-methylphenyl)-16,17-dihydroxy-17-(1-propynyl)estra-4,9-dien-3-one; m.p. 212.2–213.8° C.

1C. (11β,16α,17β)-11-(1,1'-biphenyl-4-yl)-16,17-dihydroxy-17-(1-propynyl)estra-4,9-dien-3-one; m.p. 254.8–256.2° C.

1D. 3E- and 3Z-(11β,16α,17β)-11-(4-t-butylphenyl)-16,17-dihydroxy-17-(1-pronynyl)-estra-4,9-dien-3-one oxime:

Preparation:

200 mg (0.44 mmol) of (11β,16α,17β)-11-(4-t-butylphenyl)-16,17-dihydroxy-17-(1-propynyl)-estra-4,9-dien-3-one (obtained as described in 1f) was dissolved in 1 ml pyridine. 70 mg (0.88 mmol) of hydroxylamine hydrochloride was added and the mixture was stirred at reflux temperature for 40 minutes. The mixture was poured into water, neutralised with dilute hydrochloric acid and extracted with ethyl acetate. The organic layer was washed with brine, dried over magnesium sulfate, filtered and evaporated to dryness. The crude oxime was subjected to a HPLC separation (acetonitrile/water 40/60→60/40) resulting in 39 mg 3Z-(11β,16α,17β)-11-(4-t-butylphenyl)-16,17-dihydroxy-17-(1-propynyl)-estra-4,9-dien-3-one oxime ($[\alpha]^{20}_D$=+30° (c=0.2, dioxane)) and 75 mg of 3E-(11β,16α,17β)-11-(4-t-butylphenyl)-16,17-dihydroxy-17-(1-propynyl)-estra-4,9-dien-3-one oxime ($[\alpha]^{20}_D$=+60° (c=0.6, dioxane)).

Example 2

(11β,16α,17β)-11-(4-t-butylphenyl)-16,17-dihydroxy-19,21,27-trinorcholesta-4,9-dien-20(22)-yn-3-one a) 5α,16α,17β-trihydroxy-11-[4-t-butylphenyl]-17α-hexynyl-estr-9-en-3-one 3-(cyclic 1,2-ethanediyl acetal)

1-Hexyne (2.88 g, 4 ml, 35 mmol) was dissolved in 75 ml dry THF; after cooling the solution to –20° C., 20 ml of a 1.6 M nBuLi solution was added dropwise and the mixture was stirred at −20° C. for 15 min. Then, a solution of 2.4 g 5α,16α,17β-trihydroxy-11β-[4-t-butylphenyl]-estr-9-en-3, 17-dione 3-(cyclic 1,2-ethanediyl acetal) in 50 ml THF was added dropwise and stirring was continued for 1 hr at −20 ° C.

Work-up was accomplished by pouring the mixture into saturated ammonium chloride solution, followed by extraction with ethyl acetate (2×), washing the combined organic layers with brine, drying with magnesium sulfate and evaporation of the solvents. This afforded the crude product as an oil. Trituration with diisopropyl ether afforded 800 mg of pure 5α,16α,17β-trihydroxy-11β-[4-t-butylphenyl]-17α-hexynyl-estr-9-en-3-one 3-(cyclic 1,2-ethanediyl acetal) as white crystals; m.p. 182–183° C.

b) (11β,16α,17β)-11-(4-t-butylphenyl)-16,17-dihydroxy-19,21,27-trinor-cholesta-4,9-dien-20(22)-yn-3-one The 5α,16α,17β-trihydroxy-11β-[4-t-butylphenyl]-17α-hexynyl-estr-9-en-3-one 3-(cyclic 1,2-ethanediyl acetal) obtained in the previous experiment was dissolved in 50 ml acetone; 1 ml 6N $H_2SO_4$ was added and stirring was continued for 30 min. TLC (heptanelethyl acetate 1/1) showed complete conversion of the starting material into two lipophilic products. Work-up was accomplished by addition of saturated $NaHCO_3$ solution, followed by extraction with ethyl acetate (2×), washing the combined organic layers with brine and drying over magnesium sulfate. Evaporation of the solvents gave the crude compound as an oil. Column chromatography (heptane-ethyl acetate 8/2→6/4) provided 500 mg of the desired (11β,16α,17β)-11-(4-t-butylphenyl)-16,17-dihydroxy-19,21,27-trinorcholesta-4,9-dien-20(22)-yn-3-one as amorphous white material; $[\alpha]^{20}_D$= 34.2 (c=0.5, dioxane).

The following products were prepared according to examples 2a and 2b by using 1-pentyne, 3-methoxypropyne and acetylene, respectively:

2A. (11β,16α,17β)-11-(4-t-butylphenyl)-16,17-dihydroxy-17-(1-pentynyl)estra-4,9-dien-3-one; $[\alpha]^{20}_D$=37.8 (c=1, dioxane).

2B. (11β,16α,17β)-11-(4-t-butylphenyl)-16,17-dihydroxy-17-(3-methoxy-1-propynyl)estra-4,9-dien-3-one; m.p. 171.0–171.6° C.

2C. (11β,16α,17β)-11-(4-t-butylphenyl)-16,17dihydroxy-19-norpregna-4,9-dien-20-yn-3-one; $[\alpha]^{20}_D$=46.9 (c=1, dioxane).

2D. (11β,16α,17β)-16,17-dihydroxy-11-[4-[(trifluoromethylsulphonyl)oxy]-phenyl]-17-(1-propynyl)estra-4,9-dien-3-one; $[\alpha]^{20}_D$=8.9 (c=1 dioxane).

Example 3

(11β,16α,17β)-11-(4-t-butytlhenyl)-17-hydroxy-16-methoxy-17-(1-propynyl)estra-4,9-dien-3-one a) 5α-hydroxy, 11β-[4-t-butylphenyl]-16α-methoxy-estr-9-en-3,17-dione 3-(cyclic 1,2-ethanediyl acetal)

2.0 g (4.16 mmol) 5α,16α,17β-trihydroxy-11β-[4-t-butylphenyl]-estr-9-ene-3,17-dione 3-(cyclic 1,2-ethanediyl acetal) was dissolved in 150 ml dry dichloromethane. To this solution 4.5 g 2,6-di-t-butyl-4-methylpyridine (15.75 mmol) and 1.3 g trimethyloxonium-tetrafluoroborate (8.3 mmol) were added and the solution was stirred at room temperature. After three hours, TLC analysis (heptanelethyl acetate/ethanol 10/10/1) indicated complete conversion of the starting compound. Work-up was accomplished by addition of saturated sodium bicarbonate solution, followed by extraction with dichloromethane. Evaporation of the solvent gave 2.6 g crude product, pure enough to be used in the next step.

b) 5α,17β-dihydroxy-11β-[4-t-butylphenyl]-16α-methoxy-17α-propynyl-estr-9-en-3-one-3-(cyclic 1,2-ethanediyl acetal)

The material obtained in the previous reaction was dissolved in 10 ml dry THF and added dropwise to a solution of propynyl lithium (prepared by adding propyne gas to a solution of 20 ml 1.3 M n-BuLi until the yellow colour disappeared and changed into a white suspension) at −60° C. The solution was allowed to warm to −20° C. and stirring was continued for 1 hr. Work-up was accomplished by pouring the mixture into a saturated ammonium chloride solution, followed by extraction with dichloromethane. Drying with magnesium sulfate and evaporation of the solvents gave the crude product which was purified with column chromatography (heptane/ethyl acetate 1/1). Yield: 1.15 g of the desired 5α,17β-dihydroxy-11β-[4-t-butylphenyl]-16α-methoxy-17α-propynyl-estr-9-en-3-one-3-(cyclic 1,2-ethanediyl acetal) as amorphous white material.

c) (11β,16α,17β)-11-(4-t-butylphenyl)-17-hydroxy-16-methoxy-17-(1-propynyl)-estra-4,9-dien-3-one The material (1.15 g) obtained in the previous reaction was dissolved in 20 ml acetone; 2 ml 2 N HCl were added and the mixture was stirred for 2 hrs at ambient temperature. Neutralisation with sodium bicarbonate solution and extraction with ethyl acetate provided, after washing with brine and drying over magnesium sulfate, the crude product. Column chromatography (heptanelethyl acetate 1/1) provided 700 mg of the pure title compound as amorphous material; $[\alpha]^{20}_D$=50.1 (c=0.5, dioxane).

Example 4

(11β,16α,17β)-21-chloro-11-(4-t-butylphenyl)-16, 17-dihydroxy-19-normregna-4,9-dien-20-yn-3-one a) 21chloro-11-(4-t-butylphenyl)-5α,16α,17β-trihydroxy-19-norpreg-9-en-20-yn-3-one 3-(cyclic 1,2-ethanediyl acetal)

Methyllithium (11 ml 2.2 M solution in diethyl ether) was added dropwise at 0° C. to a solution of 1.2 g trans-1,2-dichloroethene (12 mmol) in 5 ml dry diethyl ether. Stirring was continued at room temperature for 1.5 hrs. Then, a solution of 1.4 g (3 mmol) 5α,16α,17β-trihydroxy-11β-[4-t-butylphenyl]-estr-9-ene-3,17-dione 3-(cyclic 1,2-ethanediyl acetal) dissolved in 20 ml dry toluene was added dropwise and stirring was continued for 1 hr at ambient temperature. Work-up was accomplished by addition of saturated ammonium chloride solution, followed by extraction with ethyl acetate. Washing the organic layers with brine, drying over magnesium sulfate and evaporation of the solvents provided 2 g of the crude material. Column chromatography (heptane/ethyl acetate 1/1) provided 1.2 g of the desired 21-chloro-11-(4-t-butylphenyl)-5α,16α,17β-trihydroxy-19-norpregn-9-en-20-yn-3-one 3-(cyclic 1,2-ethanediyl acetal) as white amorphous material pure enough to be used in the next step.

b) (11β,16α,17β)-21-chloro-11-(4-t-butylphenyl)-16,17-dihydroxy-19-norpregna-4,9-dien-20-yn-3-one According to the procedure described in example 3c, the material obtained in the previous reaction step gave after column chromatography 460 mg of the desired (11β,16α, 17β)-21-chloro-11-(4-t-butylphenyl)-16,17-dihydroxy-19-norpregna-4,9-dien-20-yn-3-one, which could be crystallized from diethyl ether; m.p. 202.2–202.7° C. (decomposes).

Example 5

Glucocorticoid Receptors (GR) and Progesterone Receptors (PR) Binding Affinities In the following Table the receptor affinity of the compounds of the invention for glucocorticoid receptors (GR) related to progesterone receptors (PR) is presented.

The glucocorticoid affinity of the compounds was measured for glucocorticoid receptors present in intact human multiple myeloma cells and compared with the affinity of dexamethasone (according to the procedure described by H. J. Kloosterboer et al., J. Steroid Biochem., Vol. 31, 567–571 (1988)).

The progesterone affinity of the compounds was measured for cytoplasmic progesterone receptors present in human breast tumor cells and compared with the affinity of (16α)-16-ethyl-21-hydroxy-19-norpregn-4-en-3,20-dione (according to the procedure described by E. W. Bergink et al., J. Steroid Biochem., Vol. 19, 1563–1570 (1983)).

Results

| Example | GRcyt (%) | PRcyt (%) |
| --- | --- | --- |
| 1 | 372 | 3.6 |
| 1A | 317 | 2.9 |
| 2D | 136 | 1.1 |
| RU (38)486 | 193 | 36 |
| (Schering) 11 p-acetyl | 39 | 0.3 |

Compounds of the present invention were compared with 11β-(4-acetylphenyl)-16α,17β-dihydroxy-17α-(1-propynyl)estra-4,9-dien-3-one (the "11 p-acetyl" compound) disclosed in U.S. Pat. No. 5,089,635 and RU (38)486. The compounds according to the present invention showed high GRcyt while the undesired PRcyt activity was low.

What is claimed is:

1. A compound of formula I

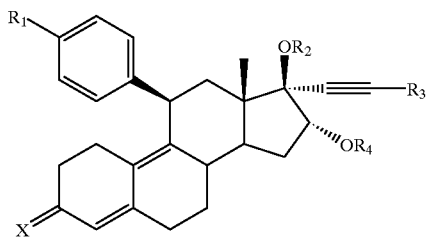

I wherein $R_1$ is $C_{1-6}$alkyl, $C_{3-6}$cycloalkyl, $C_{1-6}$alkoxy, triflate, pyridyl or phenyl where the phenyl moiety is optionally substituted by one or more substituents selected from cyano, halogen and $C_{1-4}$alkyl;

$R_2$ is hydrogen, $C_{1-6}$alkyl, 1-oxo-$C_{1-6}$alkyl or carboxy-1-oxo-$C_{1-6}$alkyl;

$R_3$ is hydrogen, halogen or $C_{1-6}$alkyl optionally substituted by one or more substituents selected form $C_{1-6}$alkoxy and halogen;

$R_4$ is hydrogen, $C_{1-6}$alkyl, 1-oxo-$C_{1-6}$alkyl or carboxy-1-oxo-$C_{1-6}$alkyl; and X is (H,OH), O or NOH;

or a pharmaceutically acceptable salt or solvate thereof.

2. A compound according to claim 1, wherein $R_1$ is phenyl, triflate or $C_{1-6}$alkyl; $R_2$ is hydrogen; $R_3$ is hydrogen, halogen, $C_{1-6}$alkyl optionally substituted by $C_{1-6}$alkoxy; $R_4$ is hydrogen or methyl; X is O; or a pharmaceutically acceptable salt or solvate thereof.

3. A compound according to claim 1, wherein $R_1$ is phenyl or $C_{1-6}$alkyl; $R_2$ is hydrogen; $R_3$ is $C_{1-6}$alkyl; $R_4$ is hydrogen or $C_{1-6}$alkyl; and X is O; or a pharmaceutically acceptable salt or solvate thereof.

4. A compound according to claim 1 wherein $R_1$ is phenyl, t-butyl, isopropyl or methyl; $R_2$ is hydrogen; $R_3$ is methyl; $R_4$ is hydrogen or methyl; and X is O; or a pharmaceutically acceptable salt or solvate thereof.

5. A compound according to claim 1, which is selected from:

(11β,16α,17β)-11-(4-t-butylphenyl)-16,17-dihydroxy-17-(1-propynyl)estra-4,9-dien-3-one;

(11β,16α,17β)-11-(4-isopropylphenyl)-16,17-dihydroxy-17-(1-propynyl)estra-4,9-dien-3-one;

(11β,16α,17β)-11-(4-methylphenyl)-16,17-dihydroxy-17-(1-propynyl)estra-4,9-dien-3-one;

(11β,16α,17β)-11-(1,1'-biphenyl-4-yl)-16,17-dihydroxy-17-(1-propynyl)estra-4,9-dien-3-one;

(11β,16α,17β)-16,17-dihydroxy-11-[4-(trifluoromethylsulfonyl)oxy]phenyl]-17-(1-propynyl)estra-4,9-dien-3-one;

or a pharmaceutically acceptable salt or solvate thereof.

6. A pharmaceutical formulation comprising a compound according to any of claims 1 to 5, together with a pharmaceutically acceptable carrier.

7. A process for the preparation of a compound of formula I as defined in any of claims 1 to 5, comprising dehydration and deprotection of a compound of formula II

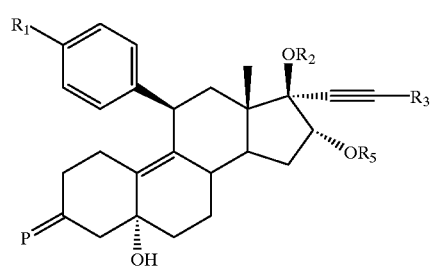

II wherein P is a protected keto group and $R_5$ is a group $R_4$ as defined in claim 1 or a suitably protected $R_4$ group;

optionally followed by treatment with a suitable reducing agent or with a suitable oximating agent; and optional conversion into a pharmaceutically acceptable salt or solvate.

8. A compound of formula II

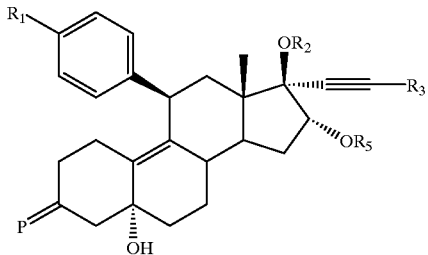

II wherein $R_1$, $R_2$ and $R_3$ are as defined in claim 1, $R_5$ is a group $R_4$ as defined in claim 1 or a suitably protected $R_4$ group and P is a protected keto group.

9. A method fox treating glucocorticoid-dependent diseases or symptoms, comprising administering to a patient in need thereof an effective amount of a compound according to any one of claims 1–5.

10. A process for preparing a pharmaceutical formulation, comprising admixing a (compound according to any one of claims 1–5 with a pharmaceutically acceptable carrier.

* * * * *

UNITED STATES PATENT AND TRADEMARK OFFICE
CERTIFICATE OF CORRECTION

PATENT NO. : 6,072,068
DATED : June 6, 2000
INVENTOR(S) : Groen, et. al.

It is certified that error appears in the above-indentified patent and that said Letters Patent is hereby corrected as shown below:

Title page, under "Attorney, Agent, or Firm", change "Mark" to --Mary--;
Column 16, line 5, please change "fox" to -- for --;
Column 16, line 11, please delete the "(" before "compound".

Signed and Sealed this

Thirteenth Day of March, 2001

Attest:

NICHOLAS P. GODICI

Attesting Officer

Acting Director of the United States Patent and Trademark Office